(12) United States Patent
Goll et al.

(10) Patent No.: US 7,060,082 B2
(45) Date of Patent: Jun. 13, 2006

(54) PERFUSION GUIDEWIRE IN COMBINATION WITH A DISTAL FILTER

(75) Inventors: Paul Goll, Woodinville, WA (US); James M. Anderson, Rockford, MN (US); Jeffrey H. Vogel, Brooklyn Park, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 473 days.

(21) Appl. No.: 10/140,404

(22) Filed: May 6, 2002

(65) Prior Publication Data
US 2003/0208225 A1   Nov. 6, 2003

(51) Int. Cl.
A61M 29/00   (2006.01)
(52) U.S. Cl. .................................... 606/200
(58) Field of Classification Search ................ 606/200
See application file for complete search history.

(56) References Cited

U.S. PATENT DOCUMENTS

| | | |
|---|---|---|
| 3,472,230 A | 10/1969 | Fogarty |
| 3,952,747 A | 4/1976 | Kimmell, Jr. |
| 3,996,938 A | 12/1976 | Clark, III |
| 4,046,150 A | 9/1977 | Schwartz et al. |
| 4,086,665 A * | 5/1978 | Poirier ..................... 623/1.44 |
| 4,425,908 A | 1/1984 | Simon |
| 4,590,938 A | 5/1986 | Segura et al. |
| 4,619,246 A | 10/1986 | Molgaard-Nielsen et al. |
| 4,650,466 A | 3/1987 | Luther |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,842,579 A | 6/1989 | Shiber |
| 4,873,978 A | 10/1989 | Ginsburg |
| 4,921,478 A | 5/1990 | Solano et al. |
| 4,921,484 A | 5/1990 | Hillstead |
| 4,926,858 A | 5/1990 | Gifford, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |

(Continued)

FOREIGN PATENT DOCUMENTS

DE   28 21 048   7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

"Endovascular Grafts, Stents Drive Interventional Radiology Growth," *Cardiovascular Device Update*, 2(3):1-12 (Mar. 1996).

(Continued)

Primary Examiner—Anhtuan T. Nguyen
Assistant Examiner—Robert Lynch
(74) Attorney, Agent, or Firm—Crompton, Seager & Tufte LLC

(57) ABSTRACT

The present invention relates generally to perfusion catheters and distal protection devices. According to an embodiment, the present invention includes a distal protection filter comprising an elongate shaft having a proximal end and a distal end, a distal protection device disposed at the distal end, a coupling member that couples the elongate shaft to the distal protection device, and a first space between the coupling member and the elongate shaft. A method of filtering debris from a blood vessel is also disclosed.

17 Claims, 3 Drawing Sheets

U.S. PATENT DOCUMENTS

| | | | |
|---|---|---|---|
| 5,049,132 A * | 9/1991 | Shaffer et al. ......... 604/101.02 |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,329,942 A | 7/1994 | Gunther et al. |
| 5,330,484 A | 7/1994 | Gunther |
| 5,354,310 A | 10/1994 | Garnie et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,458 A | 5/2000 | Engelson et al. |
| 6,068,645 A | 5/2000 | Tu |
| 6,086,605 A | 7/2000 | Barbut et al. |
| 6,102,932 A * | 8/2000 | Kurz ......................... 606/200 |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 * | 1/2001 | Khosravi et al. ............ 606/200 |
| 6,187,025 B1 * | 2/2001 | Machek ...................... 606/200 |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,066 B1 * | 6/2001 | Morgan et al. ................ 606/41 |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,726,703 B1 * | 4/2004 | Broome et al. ............. 606/200 |
| 2002/0177872 A1 | 11/2002 | Papp et al. |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |

| | | |
|---|---|---|
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/45592 A1 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |
| WO | WO 02/02162 A2 | 1/2002 |

OTHER PUBLICATIONS

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," *Surgery*, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geko*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *America Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

\* cited by examiner

… …

PERFUSION GUIDEWIRE IN COMBINATION WITH A DISTAL FILTER

FIELD OF THE INVENTION

The present invention generally relates to perfusion guidewires. More particularly, the present invention relates to perfusion guidewires used in combination with a distal protection device.

BACKGROUND OF THE INVENTION

Heart disease is a major problem in the United States and throughout the world. Conditions such as atherosclerosis result in blood vessels becoming blocked or narrowed. This blockage can result in lack of oxygenation to the heart, which has significant consequences since the heart muscle must be well oxygenated to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, stenotic debris can be separated from the wall of the blood vessel. If this debris enters the circulatory system, it could block other vascular regions including the neural and pulmonary vasculature, both of which are highly undesirable. An occlusion in the neural vasculature may cause a stroke, and an occlusion in the lungs may interfere with the oxygenation of the blood. During angioplasty procedures, stenotic debris may also break loose due to manipulation of the blood vessel. Because of this debris, a number of devices termed distal protection devices have been developed to filter out this debris.

SUMMARY OF THE INVENTION

The present invention pertains to a refinement to distal protection devices. More particularly, an embodiment of the present invention comprises a filter coupled to an elongate shaft by a coupling member. The coupling member is designed to limit coagulation of blood near the junction of the guidewire and the distal protection device.

An embodiment of the invention comprises an elongate shaft having a filter disposed proximate a distal end thereof. The filter may include devices generally adapted to prevent debris from traveling away from a treatment site during or after an intravascular procedure. The filter has at least one opening that may allow the passage of blood and substantially prevent debris (e.g., debris produced by an angioplasty or atherectomy procedure) from flowing therethrough.

The filter may be coupled to the elongate shaft by a coupling member. The coupling member may comprise a coil that is disposed about the elongate shaft. At least a portion of the coil may be coupled to the elongate shaft. An alternate coupling member may comprise a porous tube having a proximal end and a distal end.

The coupling member may be coupled to the elongate shaft and provide spaces and/or opening that permits blood flow but substantially prevent debris from passing therethrough. According to this embodiment, allowing blood through the coupling member will minimize coagulation and clotting of blood proximate the coupling member. To further limit coagulation and clotting, the coupling member, the distal protection device, and the shaft may be treated with an anti-coagulation agent.

DETAILED DESCRIPTION OF THE PREFERRED EMBODIMENTS

Figure 1:
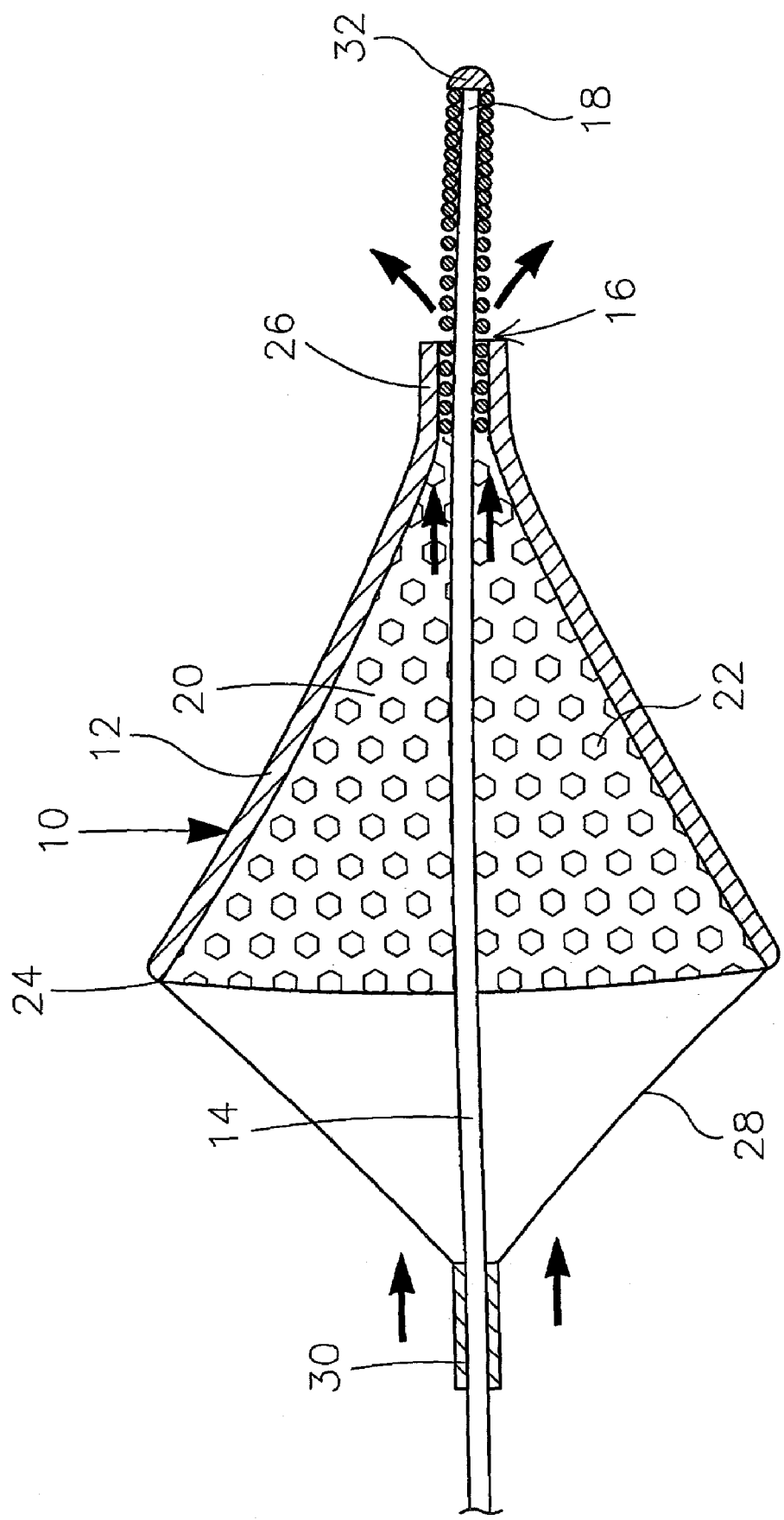
FIG. 1 is a partial cross sectional view of a distal protection filter.

The following description should be read with reference to the drawings wherein like reference numerals indicate like elements throughout the several views. The detailed description and drawings illustrate example embodiments of the claimed invention.

FIG. 1 is a partial cross sectional view of a distal protection filter 10. Distal protection filter 10 includes a filter frame 12 coupled to an elongate shaft 14 by a perfusion coupling member 16. Filter 10 may be used to filter debris from a blood vessel in conjunction with a medical procedure that produces embolic debris (e.g., angioplasty, atherectomy, etc.). Coupling member 16 may serve to minimize thrombus formation near the junction of filter frame 12 and shaft 14 by allowing fluid to perfuse therethrough.

Filter frame 12 may be disposed proximate a distal end 18 of shaft 14. A filter material 20 having at least one opening 22 may be coupled to frame 12. Filter material 20 may be constructed of a polyurethane sheet, and openings 22 may be formed in the polyurethane sheet by known laser techniques. Holes or openings are sized to allow blood flow therethrough but restrict flow of debris or emboli floating in the body lumen or cavity.

Filter 10 may be generally cone-shaped, and have a proximal mouth portion 24 a distal end 26. Distal end 26 can be narrow and/or generally "V"-shaped. Filter 10 operates between a closed collapsed profile and an open radially-expanded deployed profile for collecting debris in a body lumen. Frame includes a plurality of longitudinally-extending struts 28 extending from mouth portion 24. Struts 28 may be coupled to elongate shaft 14 by a strut coupling 30.

Elongate shaft 14 may be a guidewire that is generally metallic. For example, shaft 14 may be comprised of stainless steel, super elastic alloys (e.g., nitinol), or other suitable materials. Alternatively, shaft 14 may be comprised of a polymer or a metal-polymer composite. A distal spring tip 32 may be disposed at distal end 18. It can be appreciated that elongate shaft 14 could include an intravascular catheter, a tube having a lumen, an intravascular device, etc.

Coupling member 16 may comprise a coil that is disposed about elongate shaft 14. It should be noted that the coil of coupling member 16 is depicted in FIG. 1 (as well as analogous coils in FIGS. 2–4) in cross-section and, thus, appears as a plurality of circles. Filter 10 may be coupled to coupling member by any one of a number of methods. For example, filter 10 may be heat bonded to the coil. Alternatively, filter 10 may be coupled to coupling member by adhesive, solder, crimping, or other suitable methods.

Figure 2:
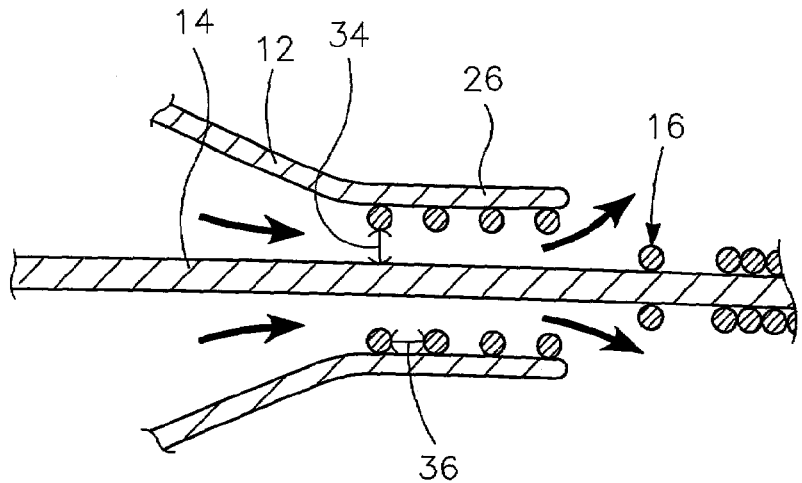
FIG. 2 is a cross sectional view of the coupling member of the filter shown in FIG. 1.
Figure 3:
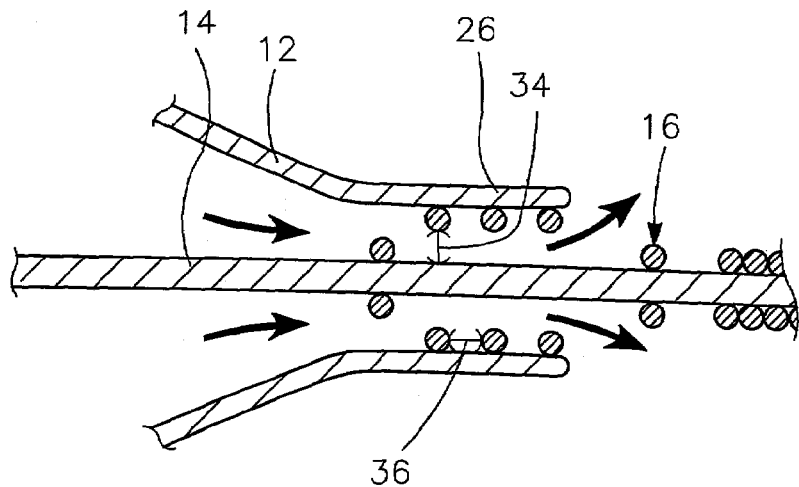
FIG. 3 is a cross sectional view of the coupling member attached to the elongate shaft in at an alternative manner.
Figure 4:
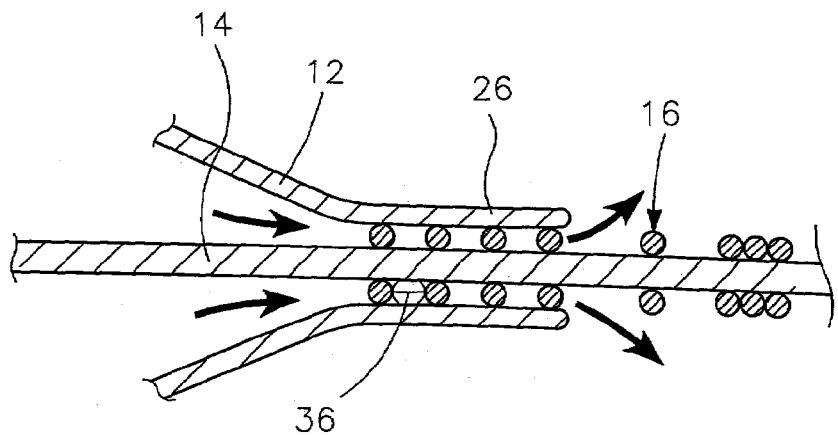
FIG. 4 is a cross sectional view of the coupling member attached to the elongate shaft in at a second alternative manner.

At least a portion of the coil (e.g., at least a portion of one winding) is attached to elongate shaft 14. For example, the coil may be attached to elongate shaft 14 at a position that is located distally of distal end 26 of filter frame 12 (FIG. 2). Alternatively, the coil may be coupled to elongate shaft 14 at a position that is near distal end 26 (FIG. 3). According to this embodiment, the coil may be further coupled to elongate shaft 14 at a location distal of distal end 26. In another alternate embodiment, the coil may be coupled to elongate shaft 14 at multiple locations along the length of elongate shaft 14 (FIG. 4). A more detailed description of the aforementioned embodiments may be found below.

FIG. 2 is a cross sectional view of coupling member 16 wherein coupling member 16 is coupled to elongate shaft 14 at a location that is distal of distal end 26 of filter frame 12. According to this embodiment, distal end 26 of filter frame 12 may be a first distance 34 away from elongate shaft 14. First distance 34 and the width of openings 22 within filter material 20 are approximately equal. First distance 34 defines a space between coupling member 16 and elongate shaft 14 to permit blood flow therethrough.

The coil of coupling member 16 has a relatively open pitch that defines a second distance 36 between individual winding of the coil. According to this embodiment, blood can flow through a space between the windings of the coil in a generally circular direction that follows the coil. Second distance 38 may be approximately equal to the width of openings 22. In an exemplary embodiment, first distance 34, second distance 36, and the width of openings 22 are all approximately equal.

It can be appreciated that blood will pass between coupling member 16 and shaft 14 through spaces therebetween and/or spaces between the individual winding of the coil. Permitting blood flow through coupling member 16 will minimize coagulation and clotting of blood proximate coupling member 16. To further minimize coagulation and clotting, coupling member 16, filter material 20, elongate shaft 14, etc. may be treated with an anti-coagulation agent. An anti-coagulation agent may include substances including, but not limited to, silicon, anti-coagulants, warfarin, nicoumalone, phenindione, heparin, low-molecular-weight heparins, anti-thrombin agents, dermatan sulfate, hirugen, argatroban, peptide chloromethyl ketone inhibitors, ancrod, anti-platelet agents, aspirin, epoprostenol, prostacyclin, ticlopidine, antibodies against the GPIIb/IIIa (glycoprotein IIb/IIb) receptor, TXA2 (thromboxane A2) synthesis inhibitors, TXA2 receptor antagonists, anti-fibrinolytic agents, tranexamic acid, aprotinin, ethamsylate, and combinations thereof. These anti-coagulation agents may be disposed at any one of the above listed locations by multiple methods including dipping any of the objects into the anti-coagulation agents.

FIG. 3 is a cross sectional view of coupling member 16 attached to elongate shaft 14 at both a location distal of distal end 26 and a location proximal of distal end 26. This additional attachment point between coupling member 16 and shaft 14 may more securely couple filter frame 12 to shaft 14. In addition, blood flow will be permitted along the windings of the coil and through the space between the coil and shaft 14.

FIG. 4 is a cross sectional view of coupling member 16 attached to elongate shaft 14 at multiple locations. According to this embodiment, the lack of spacing between frame 12 and shaft 14, will limit blood flow to being through winding of the coil. Securing coupling member 16 to shaft 14 at multiple locations may further strengthen the bond between frame 12 and shaft 14.

Figure 5:
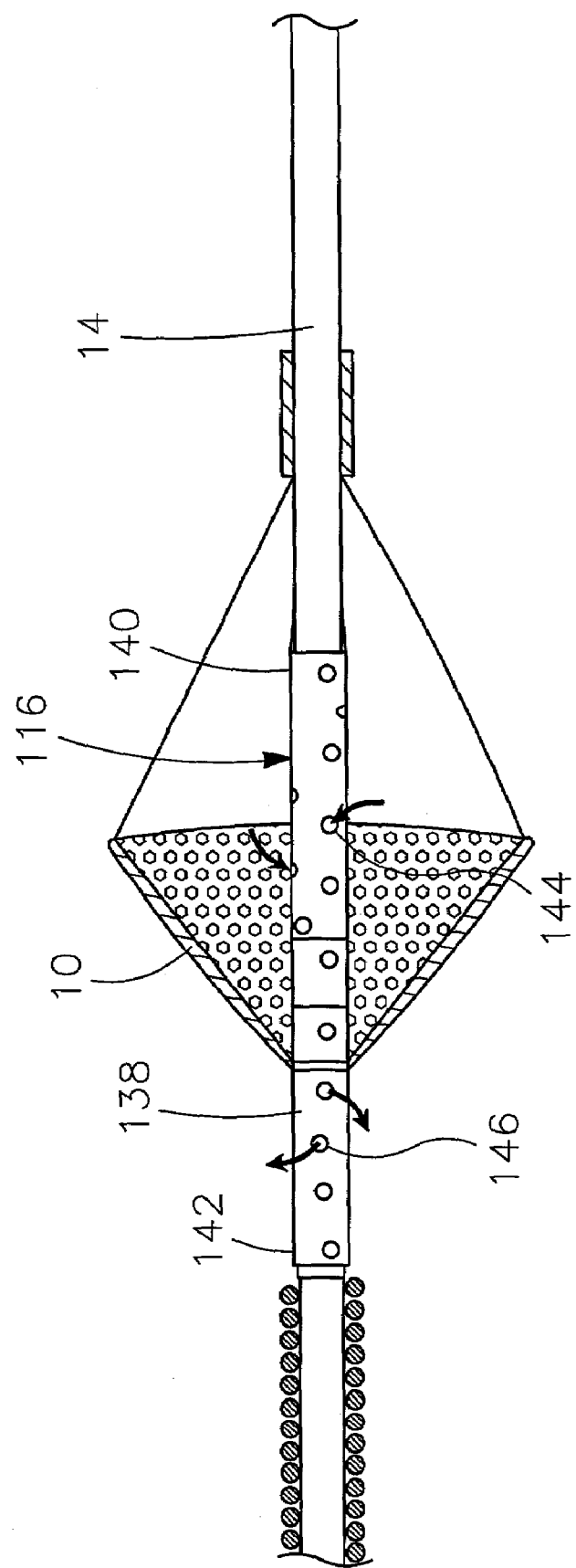
FIG. 5 is a partial cross sectional view of a distal protection filter having an alternate coupling member.

FIG. 5 is a partial cross sectional view of an alternate coupling member 116. Coupling member 116 may comprise a porous tube 138 having a proximal end 140 and a distal end 142 and is disposed over a portion of elongate shaft 14 a distance (analogous to first distance 34) away from shaft 14. The distance between tube 138 and shaft 14 defines a space therebetween.

Porous tube 138 may further comprise a first opening 144 near proximal end 140 and a second opening 146 near distal end 142. Filter frame 12 may be coupled to porous tube 138 between first opening 144 and second opening 146. The width of first opening 144 and second opening 146 may be approximately equal to the width of openings 22 in filter material 20. First opening 144 and second opening 146 are in fluid communication with one another through the space defined between shaft 14 and tube 138. It can be appreciated that porous tube 138 may include additional openings.

Similar to what is disclosed above, first opening 144 and second opening 146 may permit flow of blood but substantially prevent debris from flowing therethrough that might occlude a blood vessel. According to this embodiment, blood may enter first opening 146, migrate distally (i.e., toward distal end 18 of elongate shaft 14) within the space between shaft 14 and tube 138, and exit porous tube 138 through second opening 146. Allowing blood to pass through tube 138 may limit coagulation and clotting of blood proximate coupling member 316. Similar to what is disclosed above, coupling member 116 may be treated with substances including anti-coagulants, anti-thrombin agents, anti-platelet agents, anti-fibrinolytic agents, etc.

In addition, a method for filtering debris for a blood vessel in disclosed that utilizes any of the devices listed above. The method comprises the steps of providing elongate shaft 14 including filter 10 coupled thereto, positioning elongate shaft 14 within a blood vessel downstream of a medical procedure that may generate debris (e.g., angioplasty, atherectomy, etc.), collecting the debris with filter material 20, and allowing blood to flow through coupling member 16 (and/or coupling member 116). The method may also include the step of treating any of the above elements with an anti-coagulation agent.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A distal protection filter, comprising:
   an elongate shaft having a distal end;
   a filter coupled to the elongate shaft, the filter including a filter material and a distal end, the distal end of the filter being spaced at least in part from the elongate shaft to form a space, such that fluid can flow from proximal of the filter through the space to distal of the filter;
   further comprising a coupling member, at the distal end of the filter;
   wherein the coupling member comprises a coil;

wherein the coil is disposed a first distance away from the elongate shaft; and wherein the filter material includes one or more openings having a width and wherein the first distance and the width of the opening are approximately equal.

2. A distal protection filter, comprising:

an elongate shaft having a distal end;

a filter coupled to the elongate shaft, the filter including a filter material and a distal end, the distal end of the filter being spaced at least in part from the elongate shaft to form a space, such that fluid can flow from proximal of the filter through the space to distal of the filter;

further comprising a coupling member, at the distal end of the filter;

wherein the coupling member comprises a coil;

wherein the filter material includes one or more openings having a width;

wherein the coil is disposed a first distance away from the elongate shaft; and wherein the coil has a relatively open pitch that defines a second distance between individual windings of the coil and wherein the first distance, the second distance, and the width of the openings are approximately equal.

3. A distal protection filter, comprising:

an elongate shaft having a proximal end and a distal end;

a distal protection filter coupled to the distal end of the shaft, the filter including a filter frame having a filter material coupled thereto, the filter material including one or more openings each having a width;

a coil that couples the elongate shaft to the distal protection device;

wherein a portion of the coil is disposed a first distance from the shaft so as to define a first space adapted to permit blood flow therethrough;

wherein individual windings of the coil are separated by a second distance, the second distance defining a second space adapted to permit blood flow therethrough; and wherein the first distance, the second distance, and the width of the openings are approximately equal.

4. The perfusion guidewire in accordance with claim 3, wherein the coupling member includes a spring tip is disposed at the distal end of the elongate shaft.

5. The perfusion guidewire in accordance with claim 3, wherein the filter is coupled to the coil by heat bonding.

6. The perfusion catheter in accordance with claim 3, wherein the elongate shaft further comprises an anti-coagulation agent.

7. The perfusion catheter in accordance with claim 3, wherein the filter material further comprises an anti-coagulation agent.

8. The perfusion catheter in accordance with claim 3, wherein the coil further comprises an anti-coagulation agent.

9. A method of filtering debris from a blood vessel, comprising the steps of:

providing a distal protection filter comprising filter material and being coupled to an elongate shaft by a coupling member, the coupling member located at the distal end of the filter and the distal end of the filter being spaced at least in part from the elongate shaft to form a space such that fluid can flow from proximal of the filter through the space to distal of the filter;

wherein the coupling member is disposed a first distance away from the elongate shaft; and wherein the filter material includes one or more openings having a width and wherein the first distance and the width of the openings are approximately equal;

advancing the elongate shaft to a location downstream of a medical procedure that generates debris;

collecting the debris with the distal protection device; and allowing blood to flow through the openings within the filter material and through the space.

10. The method in accordance with claim 9, wherein the coupling member comprises a coil.

11. The method in accordance with claim 10, wherein the space is located between the coil and the shaft, and wherein the step of allowing blood to flow through the openings within the filter material and through the space includes permitting blood to flow through the space.

12. The method in accordance with claim 10, wherein the space is located between individual windings of the coil, and wherein the step of allowing blood to flow through the openings within the filter material and through the space includes permitting blood to flow through the space.

13. The method in accordance with claim 9, wherein the coupling member comprises a porous tube having a first opening disposed near a proximal end and a second opening near a distal end.

14. The method in accordance with claim 13, wherein the space is located between the first opening and the second opening, and wherein the step of allowing blood to flow through the openings within the filter material and through the space includes permitting blood to flow into the first opening, through the space, and out of the second opening.

15. The method in accordance with claim 9, further comprising the step of treating the elongate shaft with an anti-coagulation agent.

16. The method in accordance with claim 9, further comprising the step of treating the filter material an anti-coagulation agent.

17. The method in accordance with claim 9, further comprising the step of treating the coupling member with an anti-coagulation agent.

* * * * *